US012586277B2

(12) United States Patent
Arberet et al.

(10) Patent No.: US 12,586,277 B2
(45) Date of Patent: Mar. 24, 2026

(54) QUASI-NEWTON MRI DEEP LEARNING RECONSTRUCTION

(71) Applicant: Siemens Healthineers AG, Forchheim (DE)

(72) Inventors: Simon Arberet, Princeton, NJ (US); Marcel Dominik Nickel, Herzogenaurach (DE)

(73) Assignee: Siemens Healthineers AG, Forchheim (DE)

( * ) Notice: Subject to any disclaimer, the term of this patent is extended or adjusted under 35 U.S.C. 154(b) by 321 days.

(21) Appl. No.: 18/358,158

(22) Filed: Jul. 25, 2023

(65) Prior Publication Data

US 2024/0362835 A1    Oct. 31, 2024

Related U.S. Application Data

(60) Provisional application No. 63/498,354, filed on Apr. 26, 2023.

(51) Int. Cl.
| | |
|---|---|
| *G06T 11/00* | (2006.01) |
| *A61B 5/00* | (2006.01) |
| *A61B 5/055* | (2006.01) |
| *G01R 33/48* | (2006.01) |
| *G01R 33/56* | (2006.01) |

(52) U.S. Cl.
CPC ........... *G06T 11/006* (2013.01); *A61B 5/055* (2013.01); *A61B 5/7264* (2013.01); *A61B 5/742* (2013.01); *G01R 33/4818* (2013.01); *G01R 33/5608* (2013.01); *G06T 2211/424* (2013.01); *G06T 2211/441* (2023.08)

(58) Field of Classification Search
None
See application file for complete search history.

(56) References Cited

PUBLICATIONS

Hosseini et al (Unrolled Physics-Based Deep Learning MRI Reconstruction with Dense Connections using Nesterov Acceleration, 2020).*
Iyer et al (Accelerating Convergence of Proximal Methods for Compressed Sensing using Polynomials with Application to MRI, 2022).*
Sterck et al (Nonlinearly Preconditioned L-BFGS as an Acceleration Mechanism for Alternating Least Squares, with Application to Tensor Decomposition, Jun. 27, 2018).*
Uecker et al (ESPIRiT—An Eigenvalue Approach to Autocalibrating Parallel MRI, Mar. 2014).*
Aggarwal, Hemant K., Merry P. Mani, and Mathews Jacob. "MoDL: Model-based deep learning architecture for inverse problems." IEEE transactions on medical imaging 38.2 (2018): 394-405.
Bertsekas, Dimitri P. "Nonlinear programming." Journal of the Operational Research Society 48, No. 3 (1997): 334-334.

(Continued)

*Primary Examiner* — Fan Zhang

(57) ABSTRACT

Systems and methods reconstruction for a medical imaging system using a quasi-newton method. An unrolled iterative reconstruction process is used to reconstruct an image from the scan data. The unrolled iterative reconstruction process includes a plurality of cascades that include at least a data-consistency step and a regularization step. The data-consistency step is modified based at least in part on information of already calculated gradients of one or more previous cascades of the plurality of cascades using a quasi-newton computation.

13 Claims, 5 Drawing Sheets

(56)          References Cited

PUBLICATIONS

Huang, Gao, et al. "Convolutional networks with dense connectivity." IEEE transactions on pattern analysis and machine intelligence 44.12 (2019): 8704-8716.

Liang, Jingyun, et al. "Swinir: Image restoration using swin transformer." Proceedings of the IEEE/CVF international conference on computer vision. 2021. (pp. 1833-1844).

Nocedal, Jorge. "Updating quasi-Newton matrices with limited storage." Mathematics of computation 35.151 (1980): 773-782.

Ronneberger, Olaf, Philipp Fischer, and Thomas Brox. "U-net: Convolutional networks for biomedical image segmentation." In International Conference on Medical image computing and computer-assisted intervention, pp. 234-241. Springer, Cham, 2015.

Yu, Songhyun, Bumjun Park, and Jechang Jeong. "Deep iterative down-up cnn for image denoising." Proceedings of the IEEE/CVF conference on computer vision and pattern recognition workshops. 2019. 1-9.

Zhang, Kai, et al. "Practical blind denoising via swin-conv-unet and data synthesis." arXiv preprint arXiv:2203.13278 (2022).

* cited by examiner

Unrolled Iterative Reconstruction Network 300

A210 Scan Patient

A220 Reconstruct image using a preconditioner

A230 Output image

QUASI-NEWTON MRI DEEP LEARNING RECONSTRUCTION

CROSS REFERENCE TO RELATED APPLICATIONS

This application claims the benefit of the filing date under 35 U.S.C. § 119(e) of U.S. Provisional Patent Application Ser. No. 63/498,354, filed Apr. 26, 2023, which is hereby incorporated by reference in its entirety and relied upon.

FIELD

This disclosure relates to medical image reconstruction, such as reconstruction in magnetic resonance (MR) imaging.

BACKGROUND

Magnetic resonance imaging (MRI) is an important and useful imaging modality used in clinical practice. MRI is a non-invasive imaging technology that produces three dimensional detailed anatomical images. It is often used for disease detection, diagnosis, and treatment monitoring. MRI and other medical imaging modalities use reconstruction to estimate an image or real-space object from the acquired data. Image reconstruction is the process of recovering an image from raw, under-sampled signal measurements. These scans and reconstruction process may be time consuming. For example, MR imaging (MRI) is intrinsically slow, and numerous methods have been proposed to accelerate the MRI scan. One acceleration method is an under-sampling reconstruction technique (such as, for example, MR compressed sensing (CS)), where fewer samples are acquired in the MRI data space (k-space), and prior knowledge is used to restore the images in reconstruction.

Deep learning (DL) techniques improve the speed and the reconstruction quality of under-sampling techniques. Certain DL-based image reconstruction methods are based on unrolled iterative algorithms where a data-consistency step alternates with a regularization step. In order to obtain good results, multiple unrolled iterations are performed. Computational time and memory requirements are directly proportional to the number of unrolled iterations. As a consequence, the number of iterations also called cascades is usually limited to around ten as this amount provides a good balance between reconstruction image quality performance and processing time and memory requirements. Given this limited number of iterations, it is important that the data-consistency step is very efficient.

SUMMARY

By way of introduction, the preferred embodiments described below include methods, systems, instructions, and computer readable media for reconstruction in medical imaging using a quasi-newton method.

In a first aspect, a system for reconstruction of a magnetic resonance image is provided. The system includes a medical imaging scanner and an image processor. The medical imaging scanner is configured to acquire under sampled k-space data of a patient. The image processor is configured to reconstruct the magnetic resonance image from the under sampled k-space data using an unrolled iterative reconstruction process that includes a plurality of cascades that include at least a data-consistency step and a regularization step, wherein the unrolled iterative reconstruction process is based at least in part on information of already calculated gradients of one or more previous cascades of the plurality of cascades. The system may further include a display configured to display the magnetic resonance image.

In an embodiment, the under sampled k-space data is under sampled using a general pattern. The unrolled iterative reconstruction process includes a preconditioner in the data-consistency step of the unrolled iterative reconstruction process to improve a descent direction as compared to a gradient direction. The unrolled iterative reconstruction process may include a proximal optimization step that balances the data-consistency steps and the regularization steps. The system may include where the proximal optimization step is implemented with a preconditioner. The preconditioner may be applied by keeping track of intermediate results and gradients of the plurality of cascades, adapting the intermediate results and gradients locally to an optimization problem of the current cascade, computing the preconditioner using an L-BFGS method that implements a quasi-Newton method, and applying the preconditioner to the gradient direction.

In an embodiment, the under sampled k-space data is under sampled using a regular pattern. The image processor is configured to calculate coil sensitivity data from a reference scan and perform a singular value decomposition to compute a data-consistency term for the data-consistency step.

In a second aspect, a method for MR image reconstruction is provided. The method includes acquiring under sampled k-space data acquired using a general pattern; reconstructing the MR image using an unrolled iterative reconstruction comprising an inverse problem, wherein an optimization is used to solve the inverse problem, the optimization using a preconditioner applied to a gradient direction of the optimization; and outputting the reconstructed MR image. The unrolled iterative reconstruction may include a plurality of cascades each including a data consistency step and a regularization step wherein the regularization step is performed using a convolutional neural network.

The preconditioner may be computed using an L-BFGS algorithm that implements a quasi-Newton method. The L-BFGS algorithm uses gradients and inputs of previous cascades of the unrolled iterative reconstruction.

In an embodiment, a direct SENSE pseudo inverse matrix is used for initialization of the preconditioner.

In the unrolled iterative reconstruction, an image prior is weighted differently in an image space.

The method may further include applying a density-compensation function to the optimization that weights k-space coefficients differently.

In a third aspect, a method for MR image reconstruction is provided. The method includes acquiring under sampled k-space data acquired using a regular sampling pattern; reconstructing the MR image using an unrolled iterative reconstruction that is formulated as an inverse problem, wherein an optimization is used to solve the inverse problem using singular value decomposition; and outputting the reconstructed MR image. Reconstruction may use a direct sense model.

In an embodiment, the method further includes calculating a coil sensitivity data from a reference scan; decoupling an encoding matrix into aliased blocks; and performing the singular value decomposition on each of the aliased blocks.

The present invention is defined by the following claims, and nothing in this section should be taken as a limitation on those claims. Further aspects and advantages of the invention are discussed below in conjunction with the preferred embodiments and may be later claimed independently or in combination.

DETAILED DESCRIPTION

Figure 1:
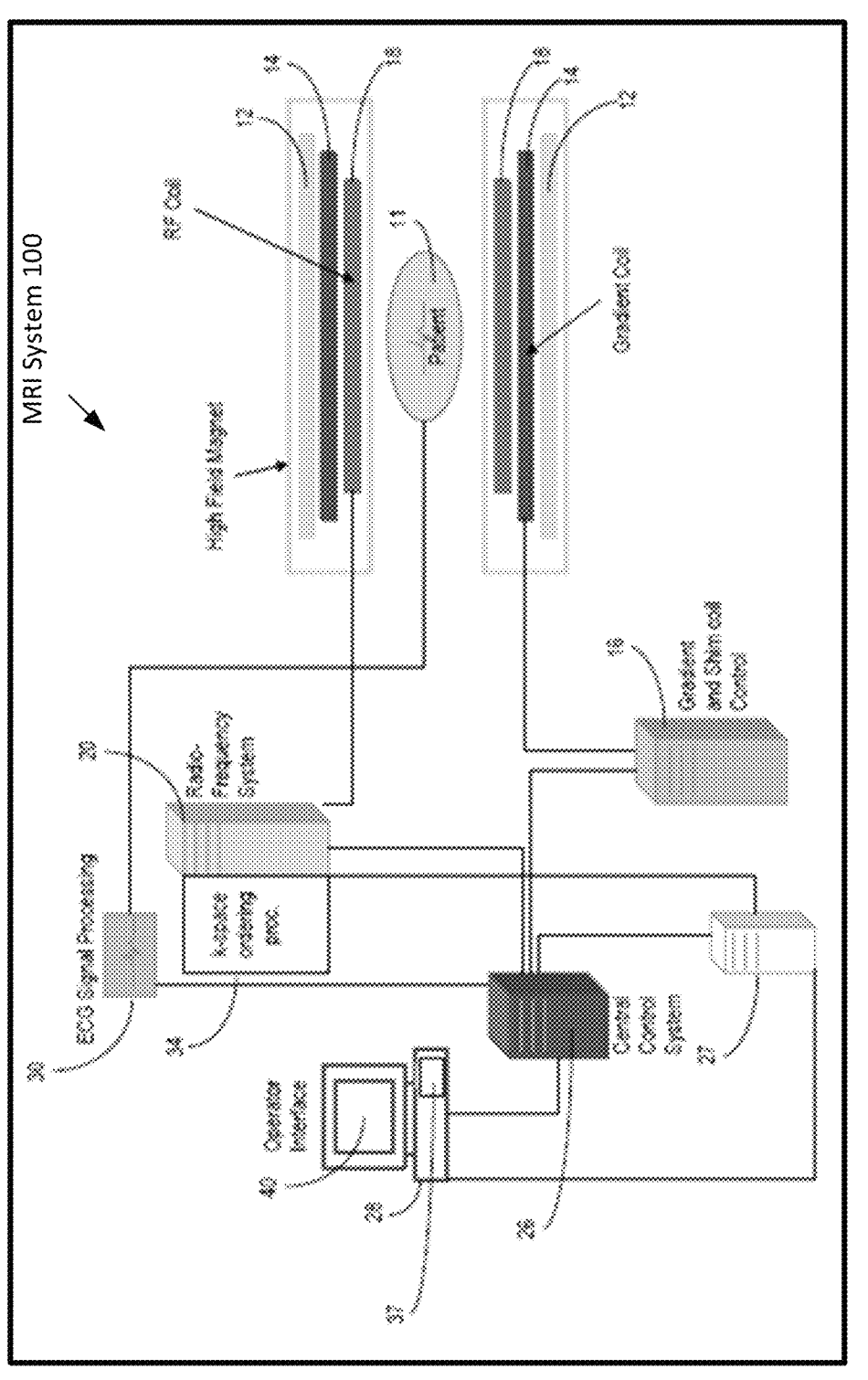
FIG. 1 depicts an example system for reconstruction in magnetic resonance (MR) imaging according to an embodiment.

Embodiments provide systems and methods of reconstruction for a medical imaging system. A patient is scanned by the medical imaging system. An unrolled iterative reconstruction process is used to reconstruct an image from the scan data. The unrolled iterative reconstruction process includes a plurality of cascades that include at least a data-consistency step and a regularization step, wherein the data-consistency step is modified based at least in part on information of already calculated gradients of one or more previous cascades of the plurality of cascades.

Image reconstruction is used for various applications. For example, some types of medical imaging perform reconstruction for imaging, such as MR, computed tomography (CT), positron emission tomography (PET), or single photon emission computed tomography (SPECT). Reconstruction may include increasing an image resolution and reducing artifacts or noise included in an image among other goals. Image reconstruction may also be used for post-processing microscopy images or video editing.

Various reconstruction algorithms are known. One example of a reconstruction algorithm employs machine learning (deep learning). Machine-learned reconstruction algorithms often show improved image quality compared to traditional reconstruction techniques.

Certain MRI deep-learning reconstruction methods alternate between some data-consistency steps and regularization steps. Such methods may be referred to as unrolled networks because their architecture is inspired by the unrolling of an iterative optimization algorithm as used in compressed sensing reconstruction. These approaches have shown superior performance compared to black box approaches where no data-consistency is enforced. In these architectures, it is important to have a correct balance between data-consistency and regularization. The balance should ideally be different in each cascade as, for example, at the beginning of the network it is important to obtain a good approximation of the image by strongly minimizing the data-consistency and then, once the image is consistent with the data, to refine the image quality with larger weight on the regularization and smaller weight on the data-consistency. Weights that are different in each region of the image may also be used as the level of noise is not consistent in the image, for example, were there is often more noise in a middle of the image as the distance to the coils is larger. Another reason to have a better data-consistency step is that some artifacts such as aliasing that often appear in the case of regular sampling patterns may be more efficiently removed if an exact inverse is applied. In the case of a purely regular sampling pattern an inverse problem that is used for optimization is called direct SENSE and may completely remove the aliasing if the coil sensitivity maps are correct. The downside of this approach however is that noise may be strong in the regions of the image far from the coils (where the g-factor is high).

In order to improve the efficiency of the data-consistency step, previous work has used Nesterov or Polyak extrapolation mechanism as well as pre-iterations, for example multiple iterations of the data-consistency step (gradient and extrapolation steps) without a regularization step in order to be able to minimize the data-consistency at the beginning of the network without too much computation. While these approaches have proven effective in some cases, the computation and storage requirements are still high, particularly for certain MR applications with higher dimensions (3D, 2D+time, 3D+time, etc.).

Embodiments provided herein disclose an improved reconstruction process that is modified in order to minimize the data-consistency more efficiently. Depending on the type of acquired MR data (for example, general sampling or regular sampling), two mechanisms may be used to reconstruct an image more efficiently.

In a first embodiment, for general (random) sampling, the data-consistency step of each cascade of the unrolled network is modified using a quasi-newton computation in order to minimize the data-consistency more efficiently. Instead of using a first order information (gradient of the data consistency at the current step), the reconstruction process approximates the second order information (Hessian), for example the curvature of the data-consistency cost function, by exploiting the information of the already calculated gradients of the previous cascades. The advantage of this process is that the number of cascades (iterations) of the unrolled network are reduced with only a negligeable increase of the computational cost of each cascade, and potentially improve the image quality of the reconstructed image by reducing aliasing artefacts. In certain embodiments, the modification includes where a pre-conditioner is built into the data-consistency step of the unrolled network to improve the descent direction as compared to the gradient direction. The pre-conditioner is inexpensive to operate in term of computation and memory. In addition, a trainable regularization term may be used in the preconditioner in order for the network to be able to find the best balance between data-consistency and regularization. The right balance depends on many factors such as the level of noise in the measurements, the g-factor maps, i.e., the conditioning of the Hessian which depends of the separability of the coils. The method learns the balance from the data during the training of the network. In addition, the data-consistency may be provided with more weight than the regularization at the beginning of the unrolled network. Subsequently, a larger regularization weight may be used towards the end of the network. A separate and trainable parameter for each data-consistency step may be used to define these weights.

In a second embodiment, in the case of regular sampling patterns, for example that are conventionally used for SENSE, GRAPPA or CAIPIRINHA, embodiments provide a more direct approach where the direct (or L2 regularized) portion of the reconstruction problem is efficiently preprocessed due to the block-diagonal structure of the system matrix.

Advantages of the improved reconstruction process include time and cost benefits by more quickly and efficiently providing more accurate images for medical diagnosis. In particular, an advantage for general sampling is provided that reduces the number of cascades of the unrolled network during reconstruction with only a negligible increase of the computational cost of each cascade, and potentially improve the image quality of the reconstructed image by reducing aliasing artefacts. The advantages for regular sampling include more constrained data consistency than gradient decent based approaches (e.g. cannot diverge), a lower number of iterations fixed in training, for example very low (N=1 is denoising), and where the last step may be user tunable λ (i.e. natural integration of denoising strength).

FIG. 1 depicts an embodiment of an MRI system 100 for reconstruction in medical imaging. The MRI system 100 is described below in general, with a following method providing other details. The MRI system 100 implements the method of FIG. 2-5 or other instructions. The example used herein is in a MR context (i.e., a MR scanner), but other types of scanners may be used (e.g., reconstruction for CT, PET, SPECT, or other medical imaging). The MRI system 100 is implemented by an MR scanner, a computer based on data obtained by MR scanning, a server, or another processor. The MRI system 100 is only exemplary, and a variety of MR scanning systems can be used to collect the MR data. The MRI scanner 100 is configured to scan a patient. The scan provides scan data in a scan domain. The system 100 scans a patient to provide k-space measurements (measurements in the frequency domain). Different sampling methods may be used.

In MRI, spatial information of the subject, such as the spin density and relaxation parameters, is encoded in the measured data in a variety of ways. Typically, a forward imaging model is used to provide a mathematical description of how the measured data is related to the spatial information (e.g., the image). A linear imaging model is used in certain implements after some approximation. This type of model may be written as $f = Am + \epsilon$, where $A: CN \rightarrow CM$ is the encoding matrix, $f \in CM$ is the acquired k-space data, $m \in CN$ is the image to be reconstructed, and e is the measurement noise, which may be modeled as complex additive Gaussian white noise under the assumption that the noise equally affects the entire frequency (i.e., all the samples in k-space). For example, with the Fourier imaging model, $A = Fu$ for the case of single-channel acquisition, $A = Fu\ S$ for the case of multichannel acquisition where S denotes the coil sensitivities and Fu the Fourier transform with under sampling. During data acquisition, the measured data f and the imaging model captured in the encoding matrix A are both known. The problem of image reconstruction is to recover the desired image m from the measurements f. There are several methods of solving for m such as obtaining the least-squares solution directly or through an iterative procedure. For example, with the single-channel acquisition, the forward MR imaging model may be formulated as a Fourier encoding. If the acquired data (k-space data) is sampled on a Cartesian grid and satisfies the Nyquist sampling criterion, the image may be reconstructed directly by applying a fast Fourier transform (FFT). Multichannel acquisition include more complicated encoding matrices but may also be reconstructed by direct matrix inversion for Cartesian sampling.

For sub-Nyquist sampling, e.g., under sampling, iterative reconstruction is used to solve the underdetermined inverse problem. additional prior information may be incorporated into the imaging model to facilitate the reconstruction, such as the spatiotemporal correlation in dynamic imaging or the quantitative model of MR parameters. Typical unrolling-based deep learning methods extend upon a compressed sensing (CS) reconstruction algorithm. Specifically, a CS reconstruction algorithm starts with the inverse problem based on the imaging model (e.g., Fourier transform) and prior constraints (e.g., sparsity and low rankness), and then applies an optimization algorithm to solve the inverse problem and find the desired image from the measured data. The optimization algorithm is iterative in nature. In unrolled deep learning methods, such an iterative reconstruction algorithm is unrolled to a deep network in which certain parameters and functions may be learned through training. The training of the deep network can be performed through the backpropagation of the training data. Embodiments provide more efficient computation of the optimization algorithm, in particular by using a quasi-newton method (for general sampling) and by using singular value decomposition (for regular sampling).

In the MRI system 100, magnetic coils 12 create a static base magnetic field in the body of patient 11 to be positioned on a table and imaged. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generate magnetic field pulse sequences. A RF (radio frequency) module 20 provides RF pulse signals to RF coil 18, which in response produces magnetic field pulses that rotate the spins of the protons in the imaged body of the patient 11 by ninety degrees, by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives MR signals, i.e., signals from the excited protons within the body as they return to an equilibrium position established by the static and gradient magnetic fields. The RF coil 18 may be a whole-body coil or may be formed from one or more local coils, at least on receive. The MR signals are detected and processed by a detector within RF module 20 and k-space component processor unit 34 to provide an MR dataset to an image processor for processing into an image (i.e., for reconstruction in the object domain from the k-space data in the scan domain). In some embodiments, the image processor is in or is the central control unit 26. In other embodiments, such as the one depicted in FIG. 1, the image processor is in a separate unit 27. An ECG synchronization signal generator 30 may provide ECG signals used for pulse sequence and imaging synchronization. A two- or three-dimensional k-space storage array of individual data elements in k-space component processor unit 34 stores corresponding individual frequency components forming an MR dataset. The k-space array of individual data elements may have a designated center, and individual data elements individually have a radius to the designated center.

The MRI system 100 is configured by the imaging protocol to scan a region of a patient 11. The magnetic field generator (comprising coils 12, 14 and 18) generates a magnetic field for use in acquiring multiple individual frequency components corresponding to individual data elements in the storage array. The k-space component processor unit 34 stores individual frequency components acquired using the magnetic field in corresponding individual data elements in, for example, an array. The imaging protocol for scanning a patient for a given examination or appointment may include different options, settings, or parameters that make up a protocol including, for example diffusion-weighted imaging (acquisition of multiple b-values, averages, and/or diffusion directions), turbo-spin-echo imaging (acquisition of multiple averages), or contrast. In an embodiment, the k-space is under sampled for more rapid scanning of the patient. The protocol is pursuant to a protocol for data acquisition with regular or irregular (general) under sampling. The reconstruction may still reconstruct a representation in the object domain from the under sampled k-space data, but the representation may be more likely to suffer from noise. In another embodiment, parallel imaging is used. Multiple local coils are used to receive the data, providing additional information for reconstruction. In yet another embodiment, Different sampling strategies may be used, for example an under-sampling technique in order to acquire and process the MR data more efficiently and quickly. One strategy may be referred to as regular or uniform under sampling along a grid pattern in k-space. With rectilinear sampling this results in a simple aliasing pattern. Another strategy is referred to as general sampling, irregular sampling, or random sampling. Compressed Sensing, for example, requires incoherence between the sensing domain and the object or any transform thereof. For this and other techniques, general sampling schedules are used. The type of sampling provides different sets of data that may be processed differently as described below in order to reconstruct an image of the patient or object. The sampling technique may be preset, for example, by the MR system 100 or may be a chosen by the operator for a particular imaging session or patient.

The central control unit 26 uses information and algorithms stored in an internal database to process the detected MR signals in a coordinated manner to generate high quality images of a selected slice(s) of the body (e.g., using the image data processor). The stored information may for example include a predetermined pulse sequence of an imaging protocol and a magnetic field gradient and strength data as well as data indicating timing, orientation, and spatial volume of gradient magnetic fields to be applied in imaging. The algorithms may include reconstruction algorithms as described below.

The MRI system 100 includes an operator interface 40, formed by an input and an output. The input may be an interface, such as interfacing with a computer network, memory, database, medical image storage, or other source of input data. The input may be a user input device, such as a mouse, trackpad, keyboard, roller ball, touch pad, touch screen, or another apparatus for receiving user input. Default, institution, facility, or group set levels may be input, such as from memory to the interface. The output is a display device but may be an interface. The final and/or intermediate images reconstructed from the scan are displayed. For example, an image of a region of the patient 11 is displayed. A generated image of the reconstructed representation for a given patient 11 is presented on a display 40 of the operator interface 40. The display 40 is a CRT, LCD, plasma, projector, printer, or other display device. The display 40 is configured by loading an image to a display plane or buffer. The display 40 is configured to display the reconstructed MR image of the region of the patient. The computer 28 of the operator interface forms a graphical user interface (GUI)

enabling user interaction with the central control unit 26 and enables user modification in substantially real time. The display processor 37 processes the magnetic resonance signals to provide image representative data for display on a display device, for example.

The central control unit 26 (i.e., controller) and/or processor 27 is an image processor 27 that reconstructs a representation of the patient from the k-space data. The image processor 27 is a general processor, digital signal processor, three-dimensional data processor, graphics processing unit, application specific integrated circuit, field programmable gate array, artificial intelligence processor, digital circuit, analog circuit, combinations thereof, or another now known or later developed device for reconstruction of an image from k-space data. The image processor 27 is a single device, a plurality of devices, or a network. For more than one device, parallel or sequential division of processing may be used. Different devices making up the image processor 27 may perform different functions, such as reconstructing by one device and volume rendering by another device. In one embodiment, the image processor 27 is a control processor or other processor of the MR scanner 100. Other image processors of the MR scanner 100 or external to the MR scanner 100 may be used. The image processor 27 is configured by software, firmware, and/or hardware to reconstruct. The instructions for implementing the processes, methods, and/or techniques discussed herein are provided on non-transitory computer-readable storage media or memories, such as a cache, buffer, RAM, removable media, hard drive, or other computer readable storage media. The instructions are executable by the processor or another processor. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the instructions set, storage media, processor or processing strategy and may be performed by software, hardware, integrated circuits, firmware, micro code, and the like, operating alone or in combination. In one embodiment, the instructions are stored on a removable media device for reading by local or remote systems. In other embodiments, the instructions are stored in a remote location for transfer through a computer network. In yet other embodiments, the instructions are stored within a given computer, CPU, GPU, or system. Because some of the constituent system components and method steps depicted in the accompanying figures may be implemented in software, the actual connections between the system components (or the process steps) may differ depending upon the manner in which the present embodiments are programmed.

The image processor 27 is configured to reconstruct a representation of a scan region, such as a region of the patient. The image processor 27 is configured to reconstruct a representation in an object domain. The representation or object in the object domain is reconstructed from the scan data in the scan domain. The scan data is a set or frame of k-space data from a scan of the patient. The object domain is an image space and corresponds to the spatial distribution of the patient. A planar or volume representation or object is reconstructed as an image representing the patient. For example, pixels values representing tissue in an area or voxel values representing tissue distributed in a volume are generated.

The reconstruction is performed, at least in part, using a machine-learned model or algorithm. The machine-learned model is formed from one or more networks and/or other machine-learned arrangements (e.g., support vector machine). For an example used herein, the machine-learned model includes one or more deep-learned neural networks included in an unrolled iterative reconstruction algorithm. As in CS, the reconstruction process using the unrolled iterative reconstruction algorithm may be formulated as a minimization problem. The goal of the optimization is to reconstruct an image set m that best matches the measured data y in the least squares sense. The network architecture of the reconstruction process utilizes data consistency, for example as exemplified by the gradient update step. Unrolled reconstructions include alternating between a data consistency step and a regularization step. The data consistency may be based on cost function of the form: $D=\|Ax-y\|^2$, where y corresponds to the acquired, under-sampled data and A the signal model that relates the target image x with the data.

In a typical unrolled reconstruction algorithm, the signal model may be based on SENSE. Sensitivity encoding (SENSE) is based on the fact that receiver sensitivity generally has an encoding effect complementary to Fourier preparation by linear field gradients. Thus, by using multiple receiver coils in parallel scan time in Fourier imaging may be considerably reduced. The problem of image reconstruction from sensitivity encoded data is formulated in a general fashion and solved for arbitrary coil configurations and k-space sampling patterns. In general the signal model may be written as: A=PUC, where P is the projection on the sampled data, U is the non-uniform Fourier transformation (or inverse non-uniform Fourier transformation depending on convention) and C the precalculated coil sensitivity maps. The ingredient for the unrolled deep learning reconstruction is then the gradient: $G=\nabla_x+D=A^+ (Ax-y)$, that is used to guide the network to consistency with the acquired data. The regularization is performed by a neural network and is a nonlinear mapping: $x'=U(x)$. The reconstruction and other networks may use various machine-learned models, such as a neural network or support vector machine. In one embodiment, the machine-learned model includes a convolutional neural network, such as an image-to-image network or U-Net.

Embodiments improve upon the unrolled reconstruction algorithm by improving the data consistency step. Mathematically, the data-consistency optimization problem to be solved at each cascade is:

$$\underset{x}{\mathrm{Argmin}}\|Ax-y\|^2 + \lambda^2\|x-x_0\|^2$$

Where $\lambda^2$ is the regularization weight, $x_0$ the prior image which is the output of the previous cascade, y is the measurement data and A is the forward imaging model which typically can be written as A=MFS, where S are the coil sensitivity maps, F the Fourier transform, and M the under-sampling mask. Solving this equation may be interpreted as a proximal optimization step. The solution, or an approximation of this proximal operation may be formulated as a linear transformation (a matrix), which may be referred to as a preconditioner.

One way to solve the data-consistency optimization problem is via an iterative algorithm, e.g., conjugate gradient descent, but as this has to be done for each cascade, this is too computationally demanding to be efficiently implemented. The data-consistency optimization problem has a closed form solution which can be written as $x \leftarrow x_0 - \alpha$ $(A^HA+\lambda^2I)^{-1}A^H(Ax_0-y)$ with $\alpha=1$, however inverting or storing the matrix $(A^HA+\lambda^2I)$ is not feasible in general.

In a first embodiment, for regular IPAT sampling, this equation may be represented as:

$$\left(A^HA + \lambda^2I\right)^{-1} = \left(1/rE^HE + \lambda^2I\right)^{-1}$$

where r is the PAT factor acceleration and E is a block diagonal matrix of size CM×N where C is the number of coils, N the number of pixels, and M=N/r the number of blocks. Each block is a matrix of size of C×r and composed of the shifted CSM coefficients. In the 2D case these blocks have the following structure:

$$E_{m=(i,j)} = \begin{pmatrix} S_0(i,j) & \cdots & S_0(i,j+(r-1)N/r) \\ \vdots & \ddots & \vdots \\ S_C(i,j) & \cdots & S_C(i,j+(r-1)N/r) \end{pmatrix}$$

where $S_0(i,j)$ is the coil sensitivity map of coil 0 at pixel (i,j).

Figure 2:
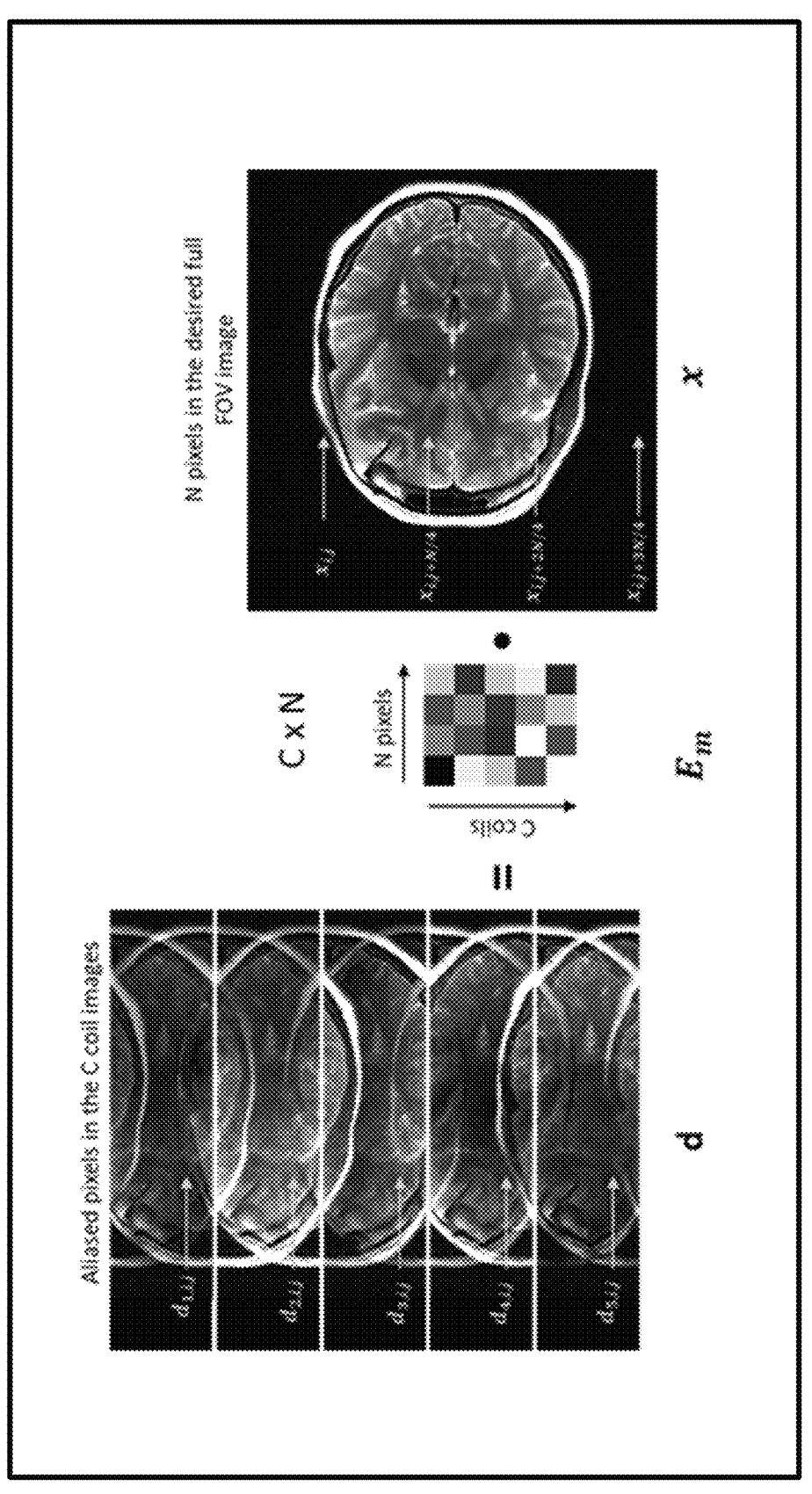
FIG. 2 depicts an example of reconstructing an image according to an embodiment.

FIG. 2 depicts a Direct Sense model with an IPAT 4 sampling pattern with 5 coils. In this model, the values of the pixels $x_{i,j}$, $x_{i,j+N/4}$, $x_{i,j+2N/4}$, $x_{i,j+3N/4}$, only depends on the values of $d_{1,i,j}$, $d_{2,i,j}$, $d_{3,i,j}$, $d_{4,i,j}$, $d_{5,i,j}$, of the aliased image via the linear matrix $E_{m=(i,j)}$ of size 5×4, or more compactly Ex=d, where d is the multicoil aliased (and cropped) image. The above equality $(A^HA+\lambda^2I)^{-1}=(1/rE^HE+\lambda^2I)^{-1}$ may be demonstrated by noticing that $E=rCF^HMFS$, with C being the cropping operator, M the sampling mask operator (assumed to be regular), and $rF^HMFC^HC=I$, where $C^H$ is the zero padding operator.

Each block $E_m$ of FIG. 2 is very small and can thus be easily inverted and inverting the all system E consists of inverting each of these blocks. To invert the regularized system, we can use the singular value decomposition (SVD) of $E=U\Sigma V^H$, and rewrite $(1/rE^HE+\lambda^2I)$ as $(1/rE^HE+\lambda^2I)=(1/rV\Sigma U^HU\Sigma V^H+\lambda^2I)=(1/rV\Sigma^2V^H+\lambda^2I)=V(\Sigma^2/r+\lambda^2I)V^H$, and thus $(A^HA+\lambda^2I)^{-1}=(1/rE^HE+\lambda^2I)^{-1}=V(1/(\Sigma^2/r+\lambda^2I))V^H$. Thus, in the particular case of regular sampling, embodiments provide a closed form solution of the regularized inverse that is easy to compute thanks to the block diagonal structure of the direct Sense model.

For general sampling, there is not a direct solution that can be computed easily to solve the data-consistency optimization problem. In a second embodiment, a quasi-Newton method is used based on the L-BFGS algorithm. The Broyden-Fletcher-Goldfarb-Shanno (BFGS) algorithm is an iterative method for solving unconstrained nonlinear optimization problems. Limited-memory BFGS (L-BFGS or LM-BFGS) is an optimization algorithm in the family of quasi-Newton methods that approximates the BFGS algorithm using a limited amount of computer memory. As in BFGS, L-BFGS uses an estimate of the inverse Hessian matrix to steer its search through variable space, but where BFGS stores a dense n×n approximation to the inverse Hessian (n being the number of variables in the problem), L-BFGS stores only a few vectors that represent the approximation implicitly.

Embodiments use a preconditioner in the data-consistency step of the unrolled network to improve the descent direction as compared to the gradient direction. To improve the performance, the cost of building the pre-conditioner is both cheap in term of computation and memory. A trainable regularization term is used in the preconditioner in order for the network to be able to find the best balance between data-consistency and regularization. The right balance depends on many factors such as the level of noise in the measurements, the g-factor maps, i.e., the conditioning of the Hessian that depends of the separability of the coils. This balance is learned during the training of the network. In addition a separate and trainable parameter for each data-consistency step is used in order to allow for more weight on the data-consistency than the regularization at the beginning of the unrolled network and a larger regularization weight towards the end of the network.

For MRI reconstruction, particularly to solve the data-consistency optimization problem, given an history of input differences $s_k = x_k - x_{k-1}$ and gradient differences $y_k = g_k - g_{k-1}$ and an initial Hessian inverse guess $H_0^{-1}$, the L-BFGS algorithm is used to compute efficiently the inverse Hessian $H^{-1}$ or more importantly compute $H^{-1}d$ for a direction d without the need to form the matrix $H^{-1}$. Hence the L-BFGS method uses a limited amount of memory and a relatively small amount of processing compared to the computation of the gradients themselves.

The inverse Hessian update of the BFGS uses the following recursion [1]:

$$H_{k+1}^{-1} = \left(I - \rho_k s_k y_k^T\right) H_k^{-1} \left(I - \rho_k s_k y_k^T\right) + \rho_k s_k s_k^T$$

The L-BFGS algorithm uses the following algorithm to compute the product $H_k^{-1}d$:

---

Input: $H_0^{-1}, \{s_k\}, \{y_k\}, d$
Output: $H_n^{-1}d$
$r \leftarrow d$
$\rho_n = (y_n^T s_n)^{-1}, \forall n$
// compute the right product
for i=n,...,1:
$\alpha_i \leftarrow \rho_i s_i^T r$
$r \leftarrow r - \alpha_i y_i$
// compute the center
$r \leftarrow H_0^{-1}r$
//compute the left product
for i=1,...,n:
$\beta \leftarrow \rho_i y_i^T r$
$r \leftarrow r - (\alpha_i - \beta)s_i$
return r
where $\{s_k\}, \{y_k\}$ are the history of the variables $s_i, 1 \le k$ and $y_i, 1 \le k$, respectively.

---

So, in order to compute an approximation of the ideal preconditioner $(A^H A + \lambda_k^2 I)^{-1}$, the gradients and inputs $x_k$ of the previous cascades are used. However, the optimization problem to be solved is different in each cascade. In each cascade k, the optimization problem to solve with the help of the L-BFGS algorithm is:

$$\underset{x}{\text{Argmin}} \|Ax - y\|^2 + \lambda_k^2 \|x - x_{k-1}\|^2,$$

The optimization problem is thus slightly different as the prior is $\|x - x_{k-1}\|^2$, where $x_{k-1}$ is the output of the previous cascade and $\lambda_k^2$ is the weight on the prior of cascade k, is different.

However, the data-consistency (DC) part $\|Ax - y\|^2$ stays the same in each cascade, which is leveraged by computing the gradients of $\|Ax - y\|^2 + \lambda_k^2 \|x - x_{k-1}\|^2$ at every cascade k, from the gradients, that were already computed, of $\|Ax - y\|^2$ at the current and previous cascades point $x_l$, $l \le k$.

The objective function in each cascade is $$J(x) = \frac{1}{2}\left(\|Ax - y\|^2 + \lambda_k^2 \|x - x_{k-1}\|^2\right),$$

then the gradient of $J(x)$ is $g_k = \nabla J(x) = A^H(Ax - y) + \lambda_k^2(x - x_{k-1})$, and its hessian is $H_J = A^H A + \lambda_k^2 I$. So given the gradient $$\widetilde{g_k} = A^H(Ax_k - y) \text{ of } \tilde{J}(x) = \frac{1}{2}\|Ax - y\|^2,$$

$$g_k = \widetilde{g_k} + \lambda_k^2(x_k - x_{k-1}) = \widetilde{g_k} + \lambda_k^2 s_k \cdot g_k$$

from $\widetilde{g_k}$ can be computed.

However, in order for L-BFGS inverse Hessian approximation to by (positive semi-definite) PSD, a sufficient condition is that $s_k^T y_k > 0$. As $s_k^T y_k = s_k^T(\widetilde{y_k} + \lambda^2 s_k) = s_k^T \widetilde{y_k} \lambda_k^2 \|s_k\|^2$, it is always possible to have this guaranty by increasing $\lambda_k^2$.

Figure 3:
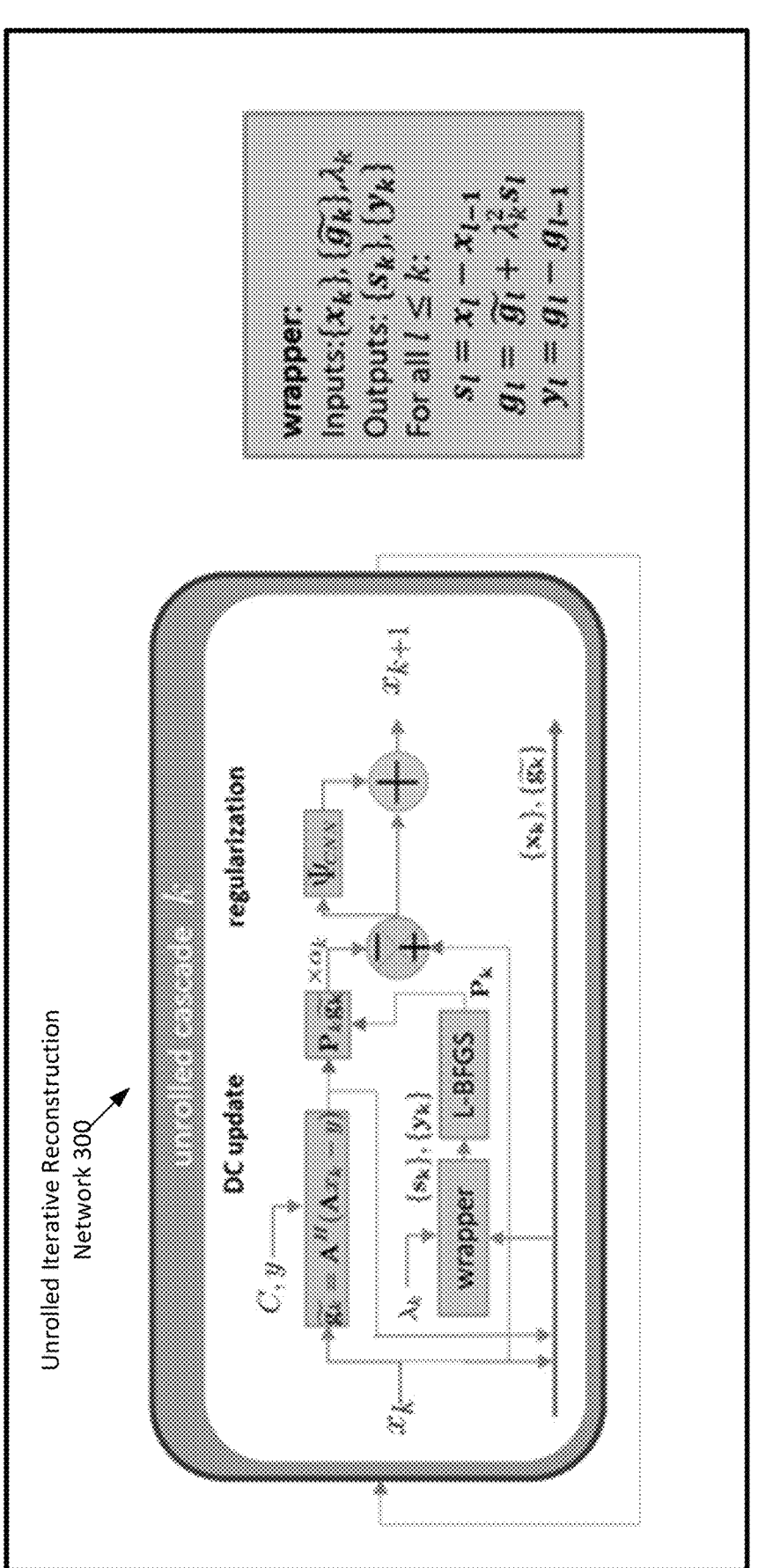
FIG. 3 depicts an example of an unrolled iterative reconstruction including a data consistency step with a L-BFGS algorithm according to an embodiment.

FIG. 3 depicts an example of an unrolled cascade of the Quasi-Newton unrolled network 300. Each unrolled cascade k of the unrolled network 300 includes keeping track of the intermediate results $x_k$ and gradients $\widetilde{g_k}$, adapting them locally to the optimization problem of the current cascade (e.g., the wrapper block in FIG. 3), then running the L-BFGS algorithm in order to compute and apply the preconditioner to the gradient direction. After the DC step a regularization step is performed with a deep learning regularization network. The architecture of the regularization network can be for example a UNet, Dense-UNet, DIDN, SwinIR, SCUnet, or any other architecture, most likely based on CNN and/or transformers architectures.

In an embodiment, an additional improvement of the L-BFGS is to rescale the initial matrix $H_0^{-1}$ by a positive scaling factor $$\widetilde{H_0^{-1}} = \frac{s_0^T y_0}{s_0^T H_0^{-1} y_0} H_0^{-1},$$

once the vector $x_1$ has been obtained and use $\widetilde{H_0^{-1}}$ instead of $H_0^{-1}$ in computing $H_1^{-1}$.

In another embodiment, the L-BFGS starts with an initialization matrix $H_0^{-1}$. The simplest initialization is to use the Identity matrix, i.e. $H_0^{-1} = I$. However, another option is to use the direct SENSE pseudo-inverse. Indeed in the case where the sampling pattern is purely regular, there is a closed form and computable inversion called direct SENSE. If the sampling pattern is closed to be regular, it thus makes sense to use this direct SENSE pseudo inverse matrix (preconditioner) as our initial $H_0^{-1}$. In certain cases, if the sampling pattern is purely regular the L-BFGS is not ideal. Rather, the regularized direct SENSE preconditioner as described in other embodiments may be used instead as it is already the inverse Hessian of the optimization problem.

There are additional alterations and options for use with the L-BFGS approach. For example, the L-BFGS approach may be extended with a density-compensation function (DCF), i.e. a diagonal matrix in the k-space domain that weights the k-space coefficients differently so that if the sampling pattern does not have a constant density (e.g. in radial or spiral sampling, or even in cartesian sampling where there are additional center lines, phase resolution, partial Fourier, etc.), the density is compensated. Density compensation is a classical step in non-cartesian sampling reconstruction. The optimization problem which needs to be solved when a DCF is used is:

$$J(x) = \frac{1}{2}\left(\left\|D^{1/2}(Ax - y)\right\|^2 + \lambda_k^2\|x - x_{k-1}\|^2\right),$$

where D is a diagonal matrix.

This results in the following gradient $\nabla J(x) = A^H D(Ax - y) + \lambda_k^2(x - x_{k-1})$ and Hessian $H_J = A^H DA + \lambda_k^2 I$. So the only difference in the implementation is the calculus of the gradients $\widetilde{g_k} = A^H D(Ax_k - y)$.

In another embodiment, the image prior may be weighted differently in the image space. If there is a noise map, and/or a g-factor map and/or a body mask, it may be beneficial to balance differently the weight between data-consistency and image prior in different regions of the image. In that case the formulation of the optimization problem becomes:

$$J(x) = \frac{1}{2}\left(\|Ax - y\|^2 + \lambda_k^2\|L(x - x_{k-1})\|^2\right),$$

with $\nabla J(x) = A^H(Ax - y) + \lambda_k^2 L^H L(x - x_{k-1})$ and $H_J = A^H A + \lambda_k^2 L^H L$, and where L and $L^H L$ are diagonal matrices with positive entries. As an example, the diagonal entries of this matrix may be a prescan normalize map, a g-factor map, a body-mask, or the product of some combination. In this case, the only thing that changes is the calculus of $g_k = \widetilde{g_k} + \lambda_k^2 L^H L(x_k - x_{k-1}) = \widetilde{g_k} + \lambda_k^2 L^H L s_k$.

The density-compensation and weighting may also be used jointly. In that case $\widetilde{g_k}$ and $g_k$ need to be updated accordingly.

When implemented, the image processor 27 is configured to input the raw data from the scanner. The image processor 27 is configured to output a representation of the object or region from which the raw data was acquired. The output representation by the image processor 27 may be a complex or real image. The output image represents the patient (i.e., a reconstructed representation). The image processor 27 may be configured to generate an MR image from the representation. Where the representation is of an area, the values of the representation may be mapped to display values (e.g., scalar values to display color values) and/or formatted for display (e.g., interpolated to a display pixel grid). Alternatively, the output representation is of display values in the display format. Where the representation is of a volume, the image processor 27 performs volume or surface rendering to render a two-dimensional image from the voxels of the volume. This two-dimensional image may be mapped and/or formatted for display as an MR image. Any MR image generation may be used so that the image represents the measured MR response from the patient. The image represents a region of the patient.

Figure 4:
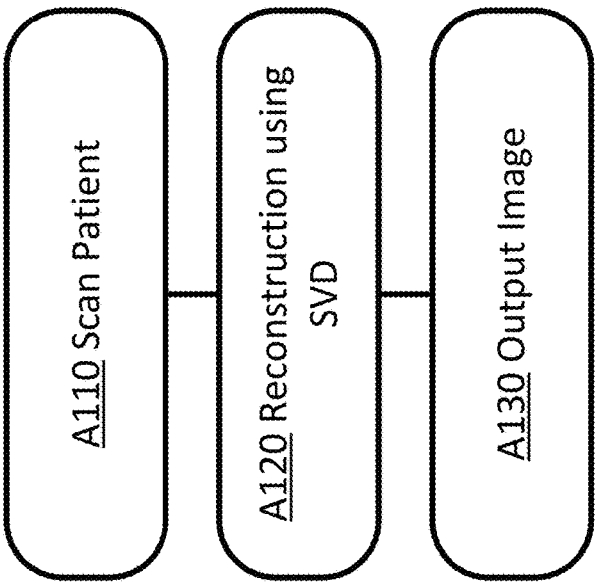
FIG. 4 depicts an example workflow for reconstruction in magnetic resonance imaging with under sampled data in a regular pattern according to an embodiment.

FIG. 4 is a flow chart diagram of one embodiment of a method for reconstruction of a medical image for a medical imaging procedure, such as reconstruction of a MR image in an MRI system 100. The method is performed by the MRI system 100 of FIG. 1 or another system and may use portions of the unrolled reconstruction algorithm 300 of FIG. 3 or other reconstruction algorithm. The medical scanner scans the patient 11 using a regular sampling technique. A representation is reconstructed from the k-space data using an unrolled iterative reconstruction algorithm including a more direct approach where the direct (or L2 regularized) part of the reconstruction problem is efficiently preprocessed due to the block-diagonal structure of the system matrix, for example using singular value decomposition (SVD) The representation may be a medical image. The image is output. In certain embodiments, a display 40 displays the image. Other components may be used, such as a remote server or a workstation performing the acquisition of the scan data, the reconstruction, and/or the display 40. The method is performed in the order shown or other orders. Additional, different, or fewer acts may be provided. For example, different preset, default, or user input settings are used to configure the scanning act 410. The output of the reconstruction process may be further processed or analyzed, for example by an addition neural network or model that is configured to further augment or process the image. As another example, the image is stored in a memory (e.g., computerized patient medical record) or transmitted over a computer network instead of or in addition to the display of act 440.

At act A110, data is acquired using a regular undersampling pattern. When MR signal k-space data are fully sampled based on the Nyquist sampling criteria, some typical high-resolution scans take five minutes, allowing time for patient and biologic movement, which negatively impacts the quality of the image. As such, under sampling techniques are used to shorten the scan time while still maintaining an acceptable level of quality. A regular undersampling pattern maintains at least some regularity in the sampling data, for example in a grid or radial pattern. This may be contrasted with general, irregular, or random sampling that is used in the method of FIG. 5 described below. The use of an under-sampling pattern may be predefined based on the MRI system 100 used or may be selected by an operator depending on the procedure and/or patient.

At act A120, reconstruction is performed using a singular value decomposition in an unrolled deep learning reconstruction. The unrolled deep learning reconstruction process includes where regularizing layers are alternated with data consistency steps within a closed network architecture that may be trained in an end-to-end fashion. The reconstruction process uses a modified version of SENSE. Sensitivity encoding (SENSE) is based on the fact that receiver sensitivity generally has an encoding effect complementary to Fourier preparation by linear field gradients. The problem of image reconstruction from sensitivity encoded data is formulated in a general fashion and solved for arbitrary coil configurations and k-space sampling patterns.

The regularized direct SENSE is calculated using, for example, coil sensitivity data from a reference scan. For SENSE the encoding matrix E decouples into aliased blocks of dimension R where:

$$x = \operatorname{argmin}_x\left(\|Ex - y\|^2 + \frac{1}{\lambda^2}\|x - z\|^2\right)$$

for each block a singular value decomposition can be performed, i.e. $E = U\Sigma V^\dagger$ $U^\dagger y$, $\Sigma$ and V are used to calculate the regularized inverse that is used to precondition the data consistency step in the reconstruction process.

The reconstruction process is performed using SENSE for example by using $U^\wedge\dagger y$, $\Sigma$ and $V$ as computed above to precondition the algorithm and calculate:

$$x_{n+1} = V\frac{1}{1+\lambda_n^2\sum}V^\dagger(\lambda_n^2 U^\dagger y + z)$$

As described previously, the inverse optimization problem may be described as:

$$(A^H A + \lambda^2 I)^{-1} = \left(\frac{1}{rE^H E} + \lambda^2 I\right)^{-1}$$

where r is the PAT factor acceleration and E is a block diagonal matrix of size CM×N where C is the number of coils, N the number of pixels, and M=N/r the number of blocks. Each block is a matrix of size of C×r and composed of the shifted CSM coefficients. In the 2D case these blocks have the following structure:

$$E_{m=(i,j)} = \begin{pmatrix} S_0(i,j) & \cdots & S_0\left(i, j+\frac{(r-1)N}{r}\right) \\ \vdots & \ddots & \vdots \\ S_C(i,j) & \cdots & S_C\left(i, j+\frac{(r-1)N}{r}\right) \end{pmatrix}$$

where $S_0(i,j)$ is the coil sensitivity map of coil 0 at pixel (i,j). This structure is illustrated in FIG. 2 and described above. In this model, the values of the pixels $x_{i,j}$, $x_{i,j+N/4}$, $x_{i,j+2N/4}$, $x_{i,j+3N/4}$, only depends on the values of $d_{1,i,j}$, $d_{2,i,j}$, $d_{3,i,j}$, $d_{4,i,j}$, $d_{5,i,j}$, of the aliased image via the linear matrix $E_{m=(i,j)}$ of size 5×4, or more compactly Ex=d, where d is the multicoil aliased (and cropped) image.

The above equality $(A^H A + \lambda^2 I)^{-1} = (1/rE^H E + \lambda^2 I)^{-1}$ may be demonstrated by noticing that $E=rCF^H MFS$, with C being the cropping operator, M the sampling mask operator (assumed to be regular), and $rF^H MFC^H C=I$, where $C^H$ is the zero padding operator.

Each block $E_m$ of FIG. 2 is very small and can thus be easily inverted and inverting the all system E consists of inverting each of these blocks. To invert the regularized system, we can use the singular value decomposition (SVD) of $E=U\Sigma V^H$, and rewrite $(1/rE^H E+\lambda^2 I)$ as $(1/rE^H E+\lambda^2 I)=(1/rV\Sigma U^H U\Sigma V^H+\lambda^2 I)=(1/rV\Sigma^2 V^H+\lambda^2 I)=V(\Sigma^2/r+\lambda^2 I)V^H$, and thus $(A^H A+\lambda^2 I)^{-1}=(1/rE^H E+\lambda^2 I)^{-1}=V(1/(1/\Sigma^2/r+\lambda^2 I))V^H$.

Thus, in the particular case of regular sampling, embodiments provide a closed form solution of the regularized inverse that is easy to compute thanks to the block diagonal structure of the direct Sense model.

In another embodiment, the approach relies on SENSE and extensions. An acceleration is adjusted by a factor R. For the aliased field-of-view there are M pixels and for the target field-of-view N=RM pixels. The Fourier-transformed, under-sampled images are denoted as $y^{(m)}$ with $c\in[0, C)$ being the coil index and $m\in[0, M)$. These are R times wrapped and need to be unfolded. The coil sensitivity maps are denoted as $A^{(m)}$ with $r\in[0, R)$ such that $m+rM\in[0, N)$. The SENSE signal model then assumes that the magnetization $x^{(m)}$ at position m+rM is related to the aliased images by:

$$y_c^{(m)} = \sum_{r=1}^{R} A_{c,r}^{(m)}, x_r^{(m)}.$$

In this notation the reconstruction decouples into M independent linear relations of the form y=Ax. Since the (pseudo-)inversion of this equation is often ill-posed, it is common to introduce an additional regularization. Here, the common Tikhonov regularization is used which leads to $x^{(n+1)}=\mathrm{argmin}_x\|Ax-y\|^2+1/\lambda 2\|x-x^{(m)}\|^2$ with a prior image $x^{(n)}$. For an initial reconstruction without known prior $x^{(0)}=0$. The equation may be solved by means of a singular value decomposition $A=U\Sigma V^\dagger$ and which provides:

$$x^{(n+1)} = V\left(1+\lambda^2\sum{}^2\right)^{-1}V^\dagger(\lambda^2 A_y^\dagger + x^{(n)}).$$

Even though the upper formulation is presented one-dimensional, it is straightforwardly extended to arbitrary dimensions. In most cases the indices may be considered as multi-indices.

For the parameter $\lambda$:

$$F_\lambda(x) = V\left(1+\lambda^2\sum{}^2\right)^{-1}V^\dagger(\lambda^2 A_y^\dagger + x)$$

and note that:

$$F_0(x) = x,$$
$$F_\infty(x) = A^+ y.$$

In other words $\lambda$ can be interpreted as a step size that interpolates from the current position to the unregularized SENSE reconstruction. In that regard it is a generalization of a gradient decent step with the advantages that the step size cannot be too large and that there is a natural scale for the step size through the singular values $\Sigma$. For small values of $\lambda$ this expression therefore also reduces to gradient decent. $F\lambda(x)$ as the data consistency step in an unrolled network 300. In a first version we perform a fixed number of recursive iterations of the form $$x^{(n+1)} = U^{(n)}(F_{\lambda_n}(x)),$$

where U(n)(x) are neural networks for regularization and also the step sizes $\lambda n$ are treated as trainable parameters.

In this implementation the network therefore has as inputs:

$$Ahy \to A_y^\dagger,$$
$$S2 \to \sum{}^2,$$
$$Vh \to V^\dagger.$$

In the Sense model, any of various machine-learned models may be used, such as a neural network or support vector machines for various tasks such as implementing a regularization function in the unrolled iterative reconstruction. In an example, an unrolled proximal gradient algorithm with Nesterov momentum includes a convolutional neural network (CNN) for regularization. To produce sharp reconstructions from input under-sampled (compressed sensing) multi-coil (parallel imaging) k-space data, the network is first trained to minimize a combined L1 and a multi-scale version of the structural similarity (SSIM) content losses between network prediction and ground truth images for regularization. Other losses may be used, such as using just the L1 loss. The same or different machine-learned model or network (e.g., CNN) is used for each or some of the unrolled iterations. The CNN for regularization may be refined, such as using a semi-supervised refinement applied in a subsequent training step where an adversarial loss is based on Wasserstein Generative Adversarial Networks (WGAN).

The learnable parameters of the unrolled network 300 are identified through training. The training data includes many sets of data, such as representations output by reconstruction and the corresponding ground truth. Tens, hundreds, or thousands of samples are acquired, such as from scans of volunteers or patients, scans of phantoms, simulation of scanning, and/or by image processing to create further samples. Many examples that may result from different scan settings, patient anatomy, scanner characteristics, or other variance that results in different samples are used. In one embodiment, an already gathered or created MR dataset is used for the training data. The samples are used in machine learning (e.g., deep learning) to determine the values of the learnable variables (e.g., values for convolution kernels) that produce outputs with minimized cost or loss across the variance of the different samples.

A computer (e.g., image processor 27) machine trains the reconstruction network. For example, the reconstruction network is machine trained using training data. In one embodiment, deep learning is used. The training learns both the features of the input data and the conversion of those features to the desired output. Backpropagation, RMSprop, ADAM, or another optimization is used in learning the values of the learnable parameters of the network (e.g., the convolutional neural network (CNN) or fully connection network (FCN)). Where the training is supervised, the differences (e.g., L1, L2, mean square error, or other loss) between the estimated output and the ground truth output are minimized.

Any architecture or layer structure for machine learning to perform an operation for separately reconstructing from subsets may be used. For example, any of the architectures may be used. The architecture defines the structure, learnable parameters, and relationships between parameters. In one embodiment, a convolutional or another neural network is used. Any number of layers and nodes within layers may be used. A DenseNet, U-Net, encoder-decoder, Deep Iterative Down-Up CNN, image-to-image and/or another network may be used. Some of the network may include dense blocks (i.e., multiple layers in sequence outputting to the next layer as well as the final layer in the dense block). Any now known or later developed neural network may be used. Any number of hidden layers may be provided between the input layer and output layer. The learning is an offline training phase where the goal is to identify an optimal set of values of learnable parameters of the model that can be applied to many different inputs. These machine-learned parameters can subsequently be used during clinical operation. Once learned, the machine-learned model is used in an online processing phase in which a reconstruction for a given patient is provided.

At act A130, an image is output. The reconstruction may output a representation or image as pixels, voxels, and/or a display formatted image in response to the input. The learned values and network architecture determine the output from the input. The output of the reconstruction, such as the output of the machine-learned model, is a two-dimensional distribution of pixels representing an area of the patient and/or a three-dimensional distribution of voxels representing a volume of the patient. The output from the last reconstruction iteration may be used as the output representation of the patient.

Other processing may be performed on the input k-space measurements before input. Other processing may be performed on the output representation or reconstruction, such as spatial filtering, color mapping, and/or display formatting. In one embodiment, the machine-learned network outputs voxels or scalar values for a volume spatial distribution as the medical image. Volume rendering is performed to generate a display image. In alternative embodiments, the machine-learned network outputs the display image directly in response to the input.

The above process may be used when a regular sampling pattern is used during acquisition. If a general, random, or irregular pattern is used, a different computation may be used to compute a preconditioner.

Figure 5:
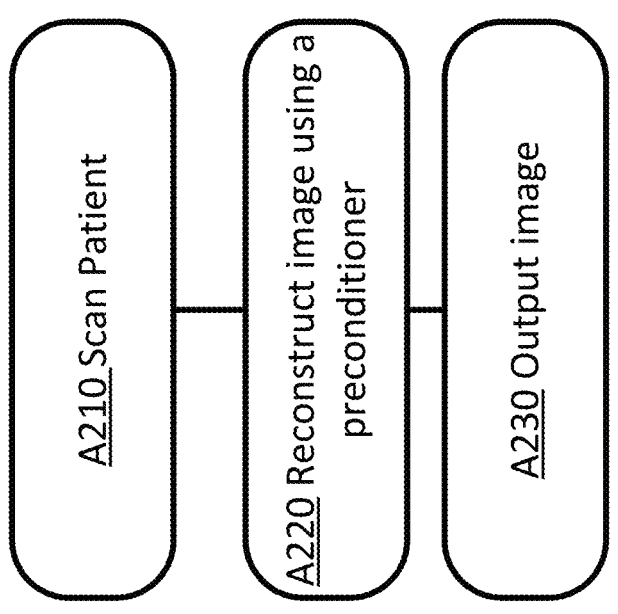
FIG. 5 depicts an example workflow for reconstruction in magnetic resonance imaging with under sampled data in a general pattern according to an embodiment.

FIG. 5 is a flow chart diagram of one embodiment of a method for reconstruction of a medical image for a medical imaging procedure, such as reconstruction of a MR image in an MRI system 100. The method is performed by the MRI system 100 of FIG. 1 or another system and may use the unrolled reconstruction algorithm 300 of FIG. 3 or other reconstruction algorithm. The medical scanner scans the patient 11 using a general (random) sampling technique. A representation is reconstructed from the k-space data using an unrolled iterative reconstruction algorithm. The representation may be a medical image, A display 40 displays the representation. Other components may be used, such as a remote server or a workstation performing the acquisition of the scan data, the reconstruction, and/or the display 40. The method is performed in the order shown or other orders. Additional, different, or fewer acts may be provided. The output of the reconstruction process may be further processed or analyzed, for example by an addition neural network or model that is configured to further augment or process the image. As another example, the image is stored in a memory (e.g., computerized patient medical record) or transmitted over a computer network instead of or in addition to the display 40.

In act A210, the MRI system 100 scans a patient. The scan is guided by a protocol, such data acquisition with general or irregular under sampling. The pulse or scan sequence scans the region of the patient, resulting in scan data for a single imaging appointment. In an MR example, a pulse sequence is created based on the configuration of the MR scanner (e.g., the imaging protocol selected). The pulse sequence is transmitted from coils into the patient. The resulting responses are measured by receiving radio frequency signals at the same or different coils. The scanning results in k-space measurements as the scan data. The sampling pattern for the scan is a general sampling pattern (irregular or random).

In act A220, an image processor 27 reconstructs a representation of the patient from the scan data using an unrolled network 300. A preconditioner in the data-consistency step of the unrolled network 300 is used to improve the descent direction as compared to the gradient direction. The preconditioner may include a trainable regularization term for the network to be able to find the best balance between data-consistency and regularization. The right balance depends on many factors such as the level of noise in the measurements, the g-factor maps, i.e. the conditioning of the Hessian which depends of the separability of the coils, and thus it is a good idea to learn it from the data during the training of the network. It is beneficial to have more weight on the data-consistency than the regularization at the beginning of the unrolled network 300 and a larger regularization weight towards the end of the network so it is preferable to have a separate and trainable parameter for each data-consistency step.

FIG. 3 described above depicts an example of a cascade in the unrolled network 300. The intermediate results $x_k$ and gradients $\widetilde{g_k}$, are tracked and adapted locally to the optimization problem of the current cascade. The L-BFGS algorithm is used to compute and apply the preconditioner to the gradient direction. The L-BFGS implements a quasi-Newton method where given an history of input differences $s_k = x_k - x_{k-1}$ and gradient differences $y_k = g_k - g_{k-1}$ and an initial Hessian inverse guess $H_0^{-1}$, the L-BFGS algorithm is used to compute efficiently the inverse Hessian $H^{-1}$ or more importantly compute $H^{-1}d$ for a direction d without the need to form the matrix $H^{-1}$. Hence the L-BFGS method uses a limited amount of memory and a relatively small amount of processing compared to the computation of the gradients themselves.

The inverse Hessian update of the BFGS uses the following recursion:

$$H_{k+1}^{-1} = (I - \rho_k s_k y_k^T)H_k^{-1}(I - \rho_k s_k y_k^T) + \rho_k s_k s_k^T$$

The L-BFGS algorithm uses the following algorithm to compute the product:

```
H_k^{-1}d:
Input: H_0^{-1},{s_k},{y_k},d
Output: H_n^{-1}d r ← d
ρ_n = (y_n^T s_n)^{-1}, ∀n
// compute the right product
for i=n,...,1: α_i ← ρ_i s_i^T r ; r ← r − α_i y_i
// compute the center
r ← H_0^{-1}r
//compute the left product
for i=1,...,n:
β ← ρ_i y_i^T r; r ← r − (α_i − β)s_i
return r
where {s_k},{y_k} are the history of the variables
s_i, l ≤ k and y_i, l ≤ k, respectively.
```

So, in order to compute an approximation of the ideal preconditioner $(A^H A + \lambda_k^2 I)^{-1}$, the gradients and inputs $x_k$ of the previous cascades are used. However, the optimization problem to be solved is different in each cascade. In each cascade k, the optimization problem to solve with the help of the L-BFGS algorithm is:

$$\operatorname*{Argmin}_{x}\|Ax - y\|^2 + \lambda_k^2\|x - x_{k-1}\|^2,$$

The optimization problem is thus slightly different as the prior is $\|x - x_{k-1}\|^2$, where $x_{k-1}$ is the output of the previous cascade and $\lambda_k^2$ is the weight on the prior of cascade k, is different.

However, the data-consistency (DC) part $\|Ax - y\|^2$ stays the same in each cascade, which is leveraged by computing the gradients of $\|Ax - y\|^2 + \lambda_k^2\|x - x_{k-1}\|^2$ at every cascade k, from the gradients, that were already computed, of $\|Ax - y\|^2$ at the current and previous cascades point $x_l$, $l \leq k$.

The objective function in each cascade is $$J(x) = \frac{1}{2}(\|Ax - y\|^2 + \lambda_k^2\|x - x_{k-1}\|^2),$$

then the gradient of J(x) is $g_k = \nabla J(x) = A^H(Ax - y) + \lambda_k^2(x - x_{k-1})$, and its hessian is $H_J = A^H A + \lambda_k^2 I$. So given the gradients $$\widetilde{g_k} = A^H(Ax_k - y)\tilde{J}(x) = \frac{1}{2}\|Ax - y\|^2,$$

$$g_k = \widetilde{g_k} + \lambda_k^2(x_k - x_{k-1}) = \widetilde{g_k} + \lambda_k^2 s_k \cdot g_k$$

from $\widetilde{g_k}$ can be computed.

However, in order for L-BFGS inverse Hessian approximation to by (positive semi-definite) PSD, a sufficient condition is that $s_k^T y_k > 0$. As $s_k^T(\widetilde{y_k} + \lambda^2 s_k) = s_k^T \widetilde{y_k} + \lambda_k^2\|^2$, it is always possible to have this guaranty by increasing $\lambda_k^2$.

After the DC step a regularization step is performed with a deep-learning network. The output of the unrolled network 300 is a representation of the object.

In act A230, the image processor 27 generates and displays an image of the object from the output representation. The resulting representation or image is then rendered to a two-dimensional display 40. A display 40 (e.g., display screen or device) displays the medical image, such as the MR image. The medical image, after or as part of any post processing, is formatted for display on the display 40. The display 40 presents the image for viewing by the user, radiologist, physician, clinician, and/or patient. The image assists in diagnosis, prognosis, and/or therapy.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description. Independent of the grammatical term usage, individuals with male, female or other gender identities are included within the term.

The invention claimed is:

1. A system for reconstruction of a magnetic resonance image, the system comprising:

a medical imaging scanner configured to acquire under sampled k-space data of a patient; and an image processor configured to reconstruct and output the magnetic resonance image from the under sampled k-space data using an unrolled iterative reconstruction process comprising an inverse problem, wherein each iteration of the unrolled iterative reconstruction process comprises a data-consistency step and a regularization step performed by a trained neural network, wherein the image processor is configured to compute the data-consistency step, for each cascade, using a quasi- Newton preconditioner that is dynamically adapted to a locally trained data-consistency loss of a current cascade by an:

initialization of the quasi-Newton preconditioner using a direct sensitivity encoding (SENSE) pseudo-inverse matrix;

an update of the quasi-Newton preconditioner using a limited-memory Broyden-Fletcher-Goldfarb-Shanno (L-BFGS) algorithm with gradients and inputs retained from previous cascades; and an application of the updated quasi-Newton preconditioner to a gradient direction that is weighted in the k-space domain by a learned density-compensation function.

2. The system of claim 1, further comprising:

a display configured to display the magnetic resonance image.

3. The system of claim 1, wherein the under sampled k-space data is under sampled using a general pattern.

4. The system of claim 3, wherein the unrolled iterative reconstruction process comprises a proximal optimization step that balances the data-consistency steps and the regularization steps.

5. The system of claim 1, wherein the under sampled k-space data is under sampled using a regular pattern.

6. The system of claim 1, wherein the image processor is configured to calculate coil sensitivity data from a reference scan and perform a singular value decomposition to compute a data-consistency term for the data-consistency step.

7. A method for MR image reconstruction, the method comprising:

acquiring, by a medical imaging scanner, under sampled k-space data acquired using a general pattern;

reconstructing the MR image from the under sampled k-space data using an unrolled iterative reconstruction comprising an inverse problem, wherein each iteration of the unrolled iterative reconstruction comprises a data-consistency step and a regularization step performed by a trained neural network, wherein the data-consistency step is computed, for each cascade, using a quasi-Newton preconditioner that is dynamically adapted to a locally trained data-consistency loss of the current cascade by:

initializing of the quasi-Newton preconditioner using a direct sensitivity encoding (SENSE) pseudo-inverse matrix;

updating the quasi-Newton preconditioner using a limited-memory Broyden-Fletcher-Goldfarb-Shanno (L-BFGS) algorithm with gradients and inputs retained from previous cascades; and applying the updated quasi-Newton preconditioner to a gradient direction that is weighted in the k-space domain by a learned density-compensation function; and outputting the reconstructed MR image.

8. The method of claim 7, wherein for the unrolled iterative reconstruction, an image prior is weighted differently in an image space.

9. The method of claim 7, further comprising applying a density-compensation function to the optimization that weights k-space coefficients differently.

10. The method of claim 7, wherein the regularization step is performed using a convolutional neural network.

11. A method for MR image reconstruction, the method comprising:

acquiring, by a medical imaging scanner, under sampled k-space data acquired using a regular sampling pattern;

reconstructing the MR image using an unrolled iterative reconstruction that is formulated as an inverse problem, wherein each iteration of the unrolled iterative reconstruction comprises a data-consistency step and a regularization step performed by a trained neural network, wherein the data-consistency step is computed, for each cascade, using a quasi-Newton preconditioner that is dynamically adapted to a locally trained data-consistency loss of the current cascade by:

initializing of the quasi-Newton preconditioner using a direct sensitivity encoding (SENSE) pseudo-inverse matrix;

updating the quasi-Newton preconditioner using a limited-memory Broyden-Fletcher-Goldfarb-Shanno (L-BFGS) algorithm with gradients and inputs retained from previous cascades; and applying the updated quasi-Newton preconditioner to a gradient direction that is weighted in the k-space domain by a learned density-compensation function; and outputting the reconstructed MR image.

12. The method of claim 11, wherein initializing the quasi-Newton preconditioner using the direct sensitivity encoding (SENSE) pseudo-inverse matrix comprises performing a singular value decomposition of an encoding matrix that represents a combination of a Fourier operator, a coil-sensitivity matrix, and a sampling operator, and computing a regularized inverse of an encoding matrix from the singular value decomposition by truncating or thresholding small singular values to improve conditioning of the quasi-Newton preconditioner.

13. The method of claim 12, further comprising:

calculating a coil sensitivity data from a reference scan;

decoupling an encoding matrix into aliased blocks; and performing the singular value decomposition on each of the aliased blocks.

*     *     *     *     *